United States Patent [19]

Olsen

[11] Patent Number: 5,156,603
[45] Date of Patent: Oct. 20, 1992

[54] SLIDE VALVE

[75] Inventor: Bent W. Olsen, Store Heddinge, Denmark

[73] Assignee: Svend Andersen Plastic Industri A/S, Haarlev, Denmark

[21] Appl. No.: 735,680

[22] Filed: Jul. 29, 1991

Related U.S. Application Data

[63] Continuation of Ser. No. 491,930, Mar. 12, 1990, abandoned.

Foreign Application Priority Data

Mar. 14, 1989 [DK] Denmark ............................ 1237/89

[51] Int. Cl.⁵ .............................................. A61M 1/00
[52] U.S. Cl. ...................... 604/323; 604/905; 251/341
[58] Field of Search ............... 604/30, 33, 118, 119, 604/167, 246, 249, 411, 902, 705, 323, 335, 350, 402; 251/311-344, 346-353, 345, 354, 147, 148, 149.1, 152, 205, 93, 149.8, 284, 296, 389, 361, 364; 128/205.11

[56] References Cited

U.S. PATENT DOCUMENTS

| | | | |
|---|---|---|---|
| 2,944,793 | 7/1960 | Conrad | 251/341 |
| 3,395,705 | 8/1968 | Hamilton | 604/119 |
| 3,685,795 | 8/1972 | Caster | 251/342 |
| 3,707,972 | 1/1973 | Villari et al. | 604/249 |
| 3,834,388 | 9/1974 | Sauer . | |
| 3,913,607 | 10/1975 | Price | 128/205.11 |
| 3,977,432 | 8/1976 | Vidal | 128/205.11 |
| 4,055,179 | 3/1976 | Manschot et al. . | |
| 4,080,965 | 3/1978 | Phillips | 604/249 |
| 4,128,209 | 12/1978 | Johnson . | |
| 4,338,933 | 7/1982 | Bayard et al. | 604/411 |
| 4,430,073 | 2/1984 | Bemis et al. | 604/249 |
| 4,522,592 | 6/1985 | Johnson | 604/902 |
| 4,595,002 | 5/1980 | Michaels et al. | 128/205.11 |
| 4,745,950 | 5/1988 | Mathieu | 604/33 |
| 4,781,702 | 11/1988 | Herrli | 604/905 |
| 4,935,010 | 6/1990 | Cox et al. | 604/905 |

Primary Examiner—David Isabella
Assistant Examiner—K. Reichle
Attorney, Agent, or Firm—Lowe, Price, Leblanc & Becker

[57] ABSTRACT

A slide valve, especially a drain valve, for collection bags, such as urine collecting bags, including an external tubular member and an internal tubular member, both members having a flow passage and being telescoped inside one another in an axially slidable manner. The external tubular member is provided with a valve body and the internal tubular member is provided with a valve seat mating the valve body of the external tubular member. The two tubular members are mutually slidable between a first position, in which the valve body sealingly engages the valve seat to prevent passage through the valve, and a second position in which passage is allowed through the valve. The external tubular member includes a first finger engaging portion at its outer circumference, and the internal tubular member comprises a second finger engaging portion situated substantially diametrically opposite the first finger engaging portion.

10 Claims, 2 Drawing Sheets

SLIDE VALVE

This application is a continuation application of application Ser. No. 07/491,930, filed Mar. 12, 1990, now abandoned.

FIELD OF THE INVENTION

The invention relates to a slide valve, especially a drain valve, for collection bags, such as urine collecting bags, comprising an external tubular member and an internal tubular member, both tubular members having a flow passage and being telescoped inside one another in an axially slidable manner, and whereby the external tubular member is provided with a valve body and the internal tubular member is provided with a valve seat mating the valve body of the external tubular member, and whereby the two tubular members are mutually slidable between a first position, in which the valve body sealingly engages the valve seat so as to shut off the passage between the two opposing ends of the valve, and a second position in which passage is allowed through the valve.

BACKGROUND ART

U.S. Pat. No. 4,055,179 discloses a two-piece valve comprising a first tubular member which is connected to the interior of a urine collecting bag at one end and at the opposite end comprises an inner tapered valve seat. A second tubular member is axially slidably positioned about the first tubular member and comprises an inner valve body. When the second tubular member is displaced, the inner valve body can be moved between a position in which it sealingly engages the valve seat inside the first tubular member so as to shut off the valve, and a position in which the valve is open. The valve of this U.S. publication and other known corresponding valves are, however, encumbered with the draw-back that the handling of the valve requires two hands, i.e. one hand gripping about the first tubular member and the other hand gripping about the second tubular member so as to open and close the valve.

SUMMARY OF THE INVENTION

It is accordingly an object of the present invention to provide a valve of the above type which is easy and hygienic to use by one hand only.

The slide valve according to the invention is characterized in that the external tubular member comprises a first finger engaging means at its outer circumference, and that the internal tubular member comprises a second finger engaging means situated substantially diametrically opposite the first finger engaging means. In this manner a valve easy to handle by one hand is obtained, the user being capable of moving the valve from the open to the closed position by gripping about the valve in such a manner that, for instance, his index finger grips the first finger engaging means and his thumb the second finger engaging means whereafter he moves the fingers and consequently the tubular members away from one another so as easily to move the valve from its closed position into its open position. Subsequently, the valve can be closed again by the user moving his fingers and consequently the tubular members in the opposite direction.

According to the invention the finger engaging means of the internal tubular member may be an engaging surface shaped directly on the outer surface of said internal tubular member, and a mating recess may be shaped in the external tubular member, whereby a particularly simple embodiment of the invention is obtained.

Furthermore, according to the invention the finger engaging means of the external tubular member may be an engaging surface shaped directly on the outer surface of the external tubular member, whereby a particularly simple embodiment of the invention is also obtained.

Moreover, according to the invention the finger engaging means of the internal tubular member may be a part preferably shaped as a segment of a cylinder on the internal tubular member, said part extending into a corresponding recess in the external tubular member. In this manner the valve is provided with a thickness facilitating the grip thereabout simultaneously with preventing a mutual turning of the two tubular members.

In addition, according to the invention the finger engaging means of the external tubular member may be a protruding part preferably shaped as a segment of a cylinder on the external tubular member with the result that the slide valve is provided with such a thickness that it can be gripped and handled in an easy and advantageous manner.

Moreover, according to the invention the finger engaging means of the internal tubular member may be a part preferably shaped as a segment of a cylinder on the internal tubular member, said part being axially hollowed when seen in a direction originating from its inner end, a connection area thereof, however, not being hollowed, whereby the cavity is adapted to receive a mating portion of the external tubular member. As a result a particularly preferred embodiment of the invention is obtained, which is very easy to handle.

Furthermore, according to the invention the part shaped as a segment of a cylinder of the first and/or the second tubular member may extend substantially across 180°. The resulting embodiment is considered particularly advantageous because the resulting finger engaging means are provided with an optimum size and can be symmetrically shaped when seen from the outside.

Finally, according to the invention the finger engaging means may comprise a finger engaging surface curving slightly inwards and presenting a friction-increasing surface structure, which results in an optimum grip about the valve, whereby said valve can be reliably and easily handled.

BRIEF DESCRIPTION OF THE DRAWINGS

Further embodiments of the invention will become apparent as the invention is explained in greater detail below with reference to the accompanying drawing, in which.

DESCRIPTION OF PREFERRED EMBODIMENTS

Figure 1:
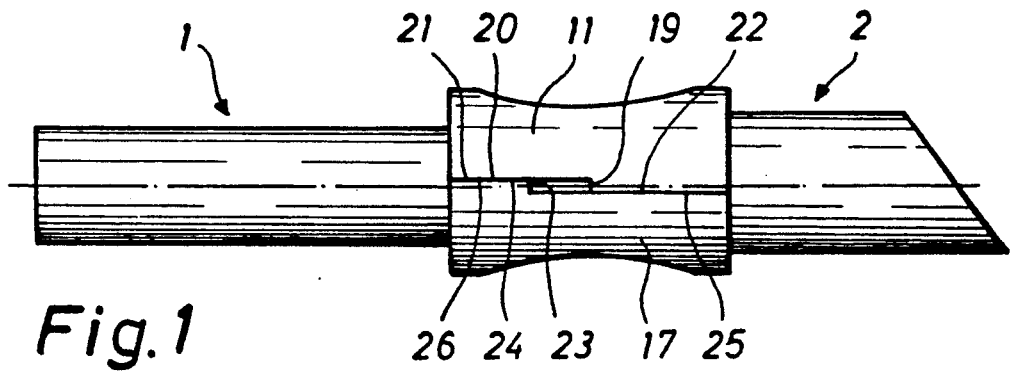
FIG. 1 is a side view of a preferred embodiment of the slide valve according to the invention.
Figure 2:
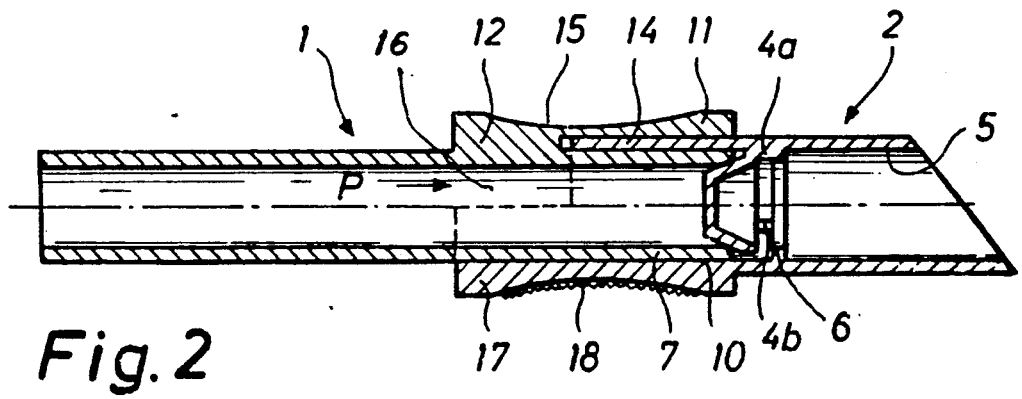
FIG. 2 is an axial sectional view through the embodiment of FIG. 1, whereby the slide valve is in the closed position.
Figure 3:
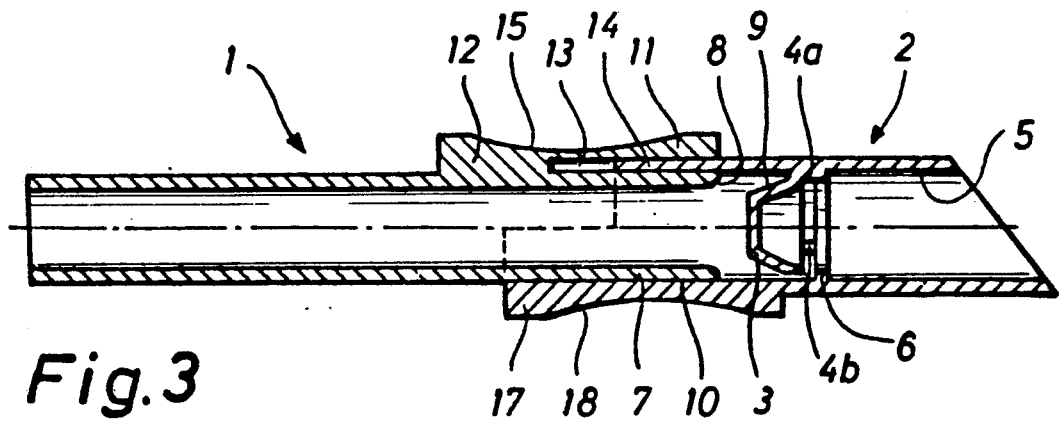
FIG. 3 is an axial sectional view through the embodiment of FIG. 1, whereby the slide valve is in the open position.

The preferred embodiment of the invention shown in FIGS. 1-3 comprises an internal tubular member 1 and an external tubular member 2, both tubular members comprising a flow passage. The external tubular member 2 is telescoped inside the internal tubular member 1 in an axially slidable manner. A frustoconical valve body 3 is situated inside the external tubular member 2, said valve body being connected to the internal surface 5 of the external tubular member 2 through three legs, only two legs 4a, 4b appearing. A passage exists between the legs 4a and 4b. An annular projection 6 is provided on the inner surface of the tubular member 2 behind the frustoconical valve body 3 when seen in the flow direction of the valve, said direction being indicated by means of an arrow P. The projection 6 serves to collect the three streams resulting from the legs 4a, 4b into a single stream. The external tubular member is obliquely cut at the outer end when seen in the flow direction through the valve.

The inner tubular part 7 of the internal tubular member 1 is at its innermost end shaped as a valve seat with a conical seat surface 8. The seat surface 8 is adapted to sealingly abut the outer conical surface 9 of the frustoconical valve body 3 so as to prevent flow through the valve.

The inner tubular part 7 of the internal tubular member 1 sealingly abuts the inner surface 5 of the external tubular member. The sealing engagement may for instance be provided by means of one or more circumferential beads (not shown) shaped on the outer surface 10 of the internal tubular member 1, said beads engaging the inner surface 5 of the outer annular member 2.

A first finger engaging means 17 is shaped on the outside of the external tubular member 2. The finger engaging means 17 is substantially semicylindrical and comprises a finger engaging surface 18 on the outside. The finger engaging surface 18 curves slightly inwards and presents a friction-increasing surface structure, such as in form of transverse waves or more or less incidental projections.

A second finger engaging means 11 is shaped on the outside of the internal tubular member 1. The second finger engaging means 11 is semicylindrical and hollowed from the valve seat end to approximately the middle of the finger engaging means 11, whereby a connection area 12 is not hollowed. The width of the cavity 3 corresponds substantially to the wall thickness of the external tubular member 2. In this manner a semicylindrical, axially extending cavity 13 is formed between the inner tubular part 7 of the internal tubular member 1 and the finger engaging means 11 of said tubular member. The cavity 13 is adapted to receive a mating portion 14 of the external tubular member 2.

The second finger engaging means 11 comprises on the outside a finger engaging surface 15 curving slightly inwards and presenting a friction-increasing structure, such as in form of transverse waves or more or less incidental projections.

The two finger engaging means 11 and 17 are in the closed position of the valve, cf. FIG. 2, situated substantially diametrically opposite one another with the result that in the area of the first finger engaging means 17 the external tubular member 2 extends more upwards on the internal tubular member 1 than in the area of the opposing semicylindrical portion 14. When seen in the flow direction P, the inner end of the portion 14 is staggered relative to the inner end of the first finger engaging means by means of a recess 16 substantially corresponding to the connecting area 12 on the second finger engaging means 11 on the internal tubular member.

When seen in the circumferential direction, the semicylindrical second finger engaging means 11 terminates to both sides in an edge 20 provided with a step 19. The edge 20 comprises a first edge portion 21 and a second edge portion 22. The first semicylindrical finger engaging means 17 terminates correspondingly in an edge 24 provided with a step 23, said edge 24 comprising a first edge portion 25 and a second edge portion 26. In this manner the first edge portion 21 of the second finger engaging means 11 abuts the second edge portion 26 of the first finger engaging means 17, and the second edge portion 22 of the second finger engaging means 11 abuts the first edge portion 25 of the first finger engaging means 17. The steps 19 and 23 are spaced in the closed position of the valve shown in FIGS. 1 and 2. The edges 20 and 24 prevent a mutual turning of the two tubular members 1 and 2, whereas the steps 19 and 23 restrict the mutual axial displacement thereof.

Figure 4:
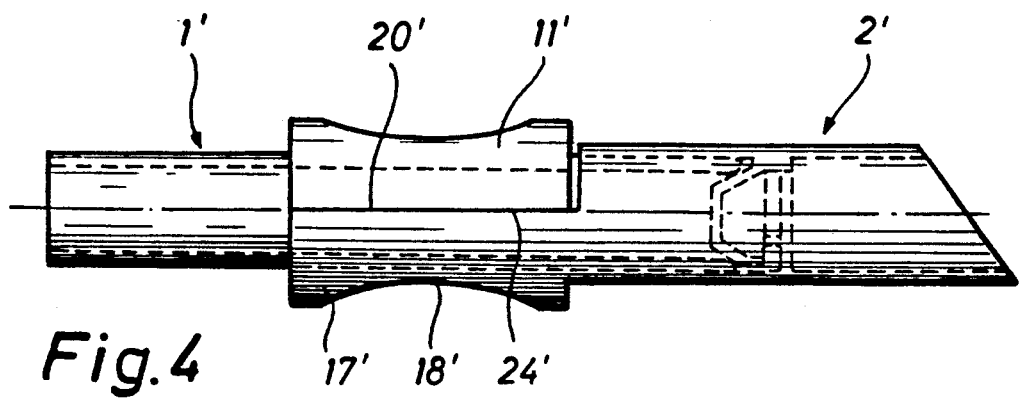
FIG. 4 is a side view of a second embodiment of the invention.
Figure 5:
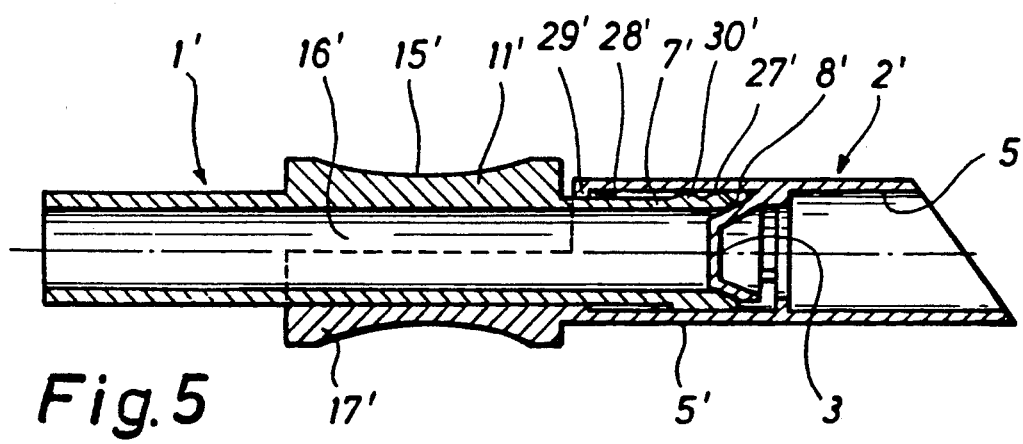
FIG. 5 is an axial sectional view through the embodiment of FIG. 4.

FIGS. 4 and 5 illustrate an alternative embodiment of the slide valve according to the invention. As this embodiment corresponds to the above embodiment in many respects, the same reference numerals have been used for the same members and provided with an indication. A first finger engaging means 17' is shaped on the outside of the external tubular member 2'. The device 17' corresponds to the finger engaging means 17 apart from the fact that it comprises a planar edge 24' when seen in the circumferential direction to both sides. The external tubular member comprises a recess 16' opposite the first finger engaging means 17'. The recess 16' corresponds substantially to a second finger engaging means 11' on the internal tubular member 1, said second finger engaging means being substantially semicylindrical. A finger engaging surface 15' is shaped on the outside of the semicylindrical finger engaging means 11' extending into the recess 16' and comprising a planar edge 20' when seen in circumferential direction to both sides. When the valve is closed the two finger engaging means 11' and 17' are situated diametrically opposite one another, and the edges 20', 24' prevent a mutual turning of the two tubular members 1', 2' but do not restrict the mutual displacement thereof.

The inner tubular part 7' of the internal tubular member 1' is surrounded by the external tubular member 2'. A sealing and guiding portion 27' is together with a clearance portion 28' provided on the inner tubular part 7', said clearance portion 28' being situated in the outward direction from the sealing and guiding portion 27' and being of a smaller diameter than said sealing and guiding portion 27'. The sealing and guiding portion 27' sealingly engages the inner surface 5' of the external tubular member 2' in addition being provided with an annular stop 29'. The stop 29' is adapted to engage the stop step 30' resulting between the sealing and guiding portion 27' and the clearance portion 28' of the internal tubular member 1' so as to restrict the mutual axial displacement of the internal tubular member 1' and the external tubular member 2' in a direction away from the closing position. The valve body and valve seat of the valve are shaped exactly as described in connection with FIGS. 1-3.

Figure 6:
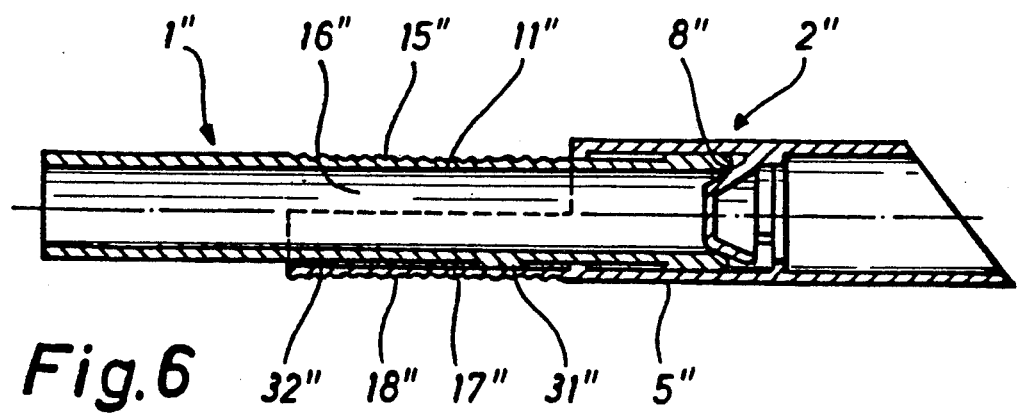
FIG. 6 is an axial sectional view through a third embodiment of the invention.

FIG. 6 illustrates a third embodiment of the invention. The third embodiment is completely identical with the embodiment of FIGS. 4 and 5 apart from the feature that the finger engaging means 11″, 17″ are formed by engaging surfaces 15″, 18″ directly shaped on the outer surface of the internal tubular member 1″ and on the outer surface of the external tubular member 2″. In addition, the third embodiment involves a knob 31″ projecting from the outer surface of the internal tubular member 1″ for preventing the mutual turning of the two tubular members 1″, 2″. The knob 31″ engages an axially extending groove 32″ shaped in the inner surface of the external tubular member 2″. The external tubular member 2″ comprises a recess 16″ opposite its finger engaging surface 18″, said recess 16″ mating the finger engaging surface 15 on the internal tubular member 1″.

The two tubular members of all three embodiments of the invention are preferably made of plastics, such as polyvinylchloride or polyethylene, and manufactured as integral parts by injection moulding.

The invention may be altered in many ways without thereby deviating from the scope thereof. Thus the finger engaging means may be arranged such on the respective members that said means substantially oppose one another in the open position of the valve and are mutually staggered in the closed position of the valve.

Though the valve primarily is to be mounted on a collection bag, such as a urine collecting bag, it can, however, also be used for other purposes, such as connected to a soft plastic tube and used as a shut off valve.

I claim:

1. A two-piece valve comprising an external tubular member having a flow passage therethrough in which a valve body means is arranged, and an inner end and an internal tubular member having a flow passage therethrough including a valve seat means at an inner end thereof, said external and internal tubular members each also having an outer end portion, one of said outer end portions of said external and internal tubular members defining an inlet of said two-piece valve and the other of said outer end portions of said external and internal tubular members defining an outlet of said two-piece valve, said external tubular member and said internal tubular member being slidably telescopically engaged with one another with said inner end of the internal tubular member being slidably positioned within the inner end of said external tubular member so that said flow passages of said internal and external tubular members define a continuous flow passage from said inlet to said outlet and so as to allow mutual sliding of said external and internal tubular members between a first position in which said engages said valve seat means so as to close the continuous flow passage between said inlet and said outlet, and a second position in which said continuous flow passage between said inlet and said outlet is open, said external tubular member further includes a first finger engaging means at a peripheral portion thereof, and said internal tubular member includes a second finger engaging means at a peripheral portion thereof which is substantially diametrically opposed to said first finger engaging means when said external and internal tubular members are in or between said first and second positions.

2. A valve as in claim 1, wherein said second finger engaging means of said internal tubular member is an engaging surface shaped directly on an outer surface of said internal tubular member, and a mating recess is provided in said external tubular member.

3. A valve as in claim 1, wherein said first finger engaging means of said external tubular member comprises an engaging surface shaped direclty on an outer surface of said external tubular member.

4. A valve as in claim 1, wherein said second finger engaging means of said internal tubular member comprises a semi-cylindrically shaped element on said internal tubular member.

5. A valve as in claim 1, wherein said first finger engaging means of the external tubular member comprises a semi-cylindrically shaped element on said external tubular member.

6. A valve as in claim 1, wherein said second finger engaging means of said internal tubular member comprises a semi-cylindrically shaped element on said internal tubular member, said element including a semi-annular hollow portion for receiving a mating portion of said external tubular member.

7. A valve as in claim 1, wherein at least one of said first and second finger engaging means comprises a semi-cylindrically shaped element on the respective tubular member which extends substantially 180° along the circumference of said respective tubular member.

8. A valve as in claim 1, wherein at least one of said first and second finger engaging means comprise a finger engaging surface which curves slightly inwards and includes a friction-increasing surface structure.

9. A valve as in claim 1, wherein said two tubular members comprise cooperating guide means which prevent relative turning of said tubular members.

10. A valve as in claim 1, wherein said two tubular members comprise cooperating stop means restricting the relative mutual sliding of said tubular members in a direction away from said first position.

* * * * *